(12) United States Patent
Gao (10) Patent No.: US 6,274,383 B1
(45) Date of Patent: Aug. 14, 2001

(54) METHODS FOR SYNTHESIZING LIBRARIES OF DIHYDRO-QUINAZOLINONES

(75) Inventor: Yun Gao, Southborough, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 08/990,938

(22) Filed: Dec. 15, 1997

(51) Int. Cl.$^7$ .................................................. C07D 239/72
(52) U.S. Cl. ........................ 436/518; 544/283; 544/284; 544/286; 544/287; 544/289; 436/536; 436/518
(58) Field of Search .................................... 436/536, 518; 544/283, 284, 286, 287, 289

(56) References Cited

U.S. PATENT DOCUMENTS

| | | | | |
|---|---|---|---|---|
| 3,862,949 | * | 1/1975 | Shetty | 260/256.5 |
| 4,386,002 | * | 5/1983 | Roberts . | |
| 5,143,854 | | 9/1992 | Pirrung et al. | 436/518 |
| 5,783,577 | * | 7/1998 | Houghten et al. | 514/247 |
| 6,184,377 | * | 2/2001 | Gao | 544/234 |

FOREIGN PATENT DOCUMENTS

| 1952-896 | * | 7/1970 | (DE) . |
|---|---|---|---|
| 51-131828 | * | 11/1976 | (JP) . |

OTHER PUBLICATIONS

Lemzoff, C.C., The use of insoluble polymer supports in general organic synthesis. Accounts of Chemical Research. 11 327–333, 1978.*

March, J. Advanced Organic Chemistry. 4th ed. Jhn Whiley and Sons. New York. pp. 896–897, 1992.*

Luk'yanov et al., Russ. Chem. Bull. (English Translation of Izv. Akad. Nauk, Ser. Khim.), 46(1), 110–112, 1997.*

Schapira et al., J. Heterocyclic Chem., 9, 569–576, 1976.*

Christie et al., J. Chem. Soc. Perkin Trans., 2779–2783, 1985.*

G. Bonola & E. Sianesi, "2,3–Dihydro– 4(1H)–quinazolinone Derivatives," *J. Med. Chem.*, 13, 329–332, 1970.

R. M. Christie & S. Moss, "Cyclisation of Schiff Bases containing Amide or Hydroxamic Acid Groups to 1,2–Dihydroquinazolin–4–ones; Thermal Decomposition Reactions of the 1,2–Dihydroquinazolin–4–ones," *J. Chem. Soc. Perkin Trans. I*, 2779–2783, 1985.

* cited by examiner

*Primary Examiner*—Jyothsna Venkat
*Assistant Examiner*—Grace Hsu
(74) *Attorney, Agent, or Firm*—Dana M. Gordon; Foley Hoag & Eliot LLP (57) ABSTRACT

Synthetic methods for solution and solid-phase synthesis of combinatorial libraries of dihydro-quinazolinones, including synthesis of 2,3-dihydro-3-alkoxy-4(1H)-quinazolinones or 2,3-dihydro-3-hydroxy-4(1H)-quinazolinones via the Lewis-acid catalyzed reaction of an appropriate 2-aminobenzamide with an aldehyde at ambient temperature performed on a solid support or in solution.

10 Claims, 3 Drawing Sheets

METHODS FOR SYNTHESIZING LIBRARIES OF DIHYDRO-QUINAZOLINONES

1. FIELD OF THE INVENTION

The present invention is directed to solution and solid phase syntheses of dihydro-quinazolinones.

2. BACKGROUND OF THE INVENTION

There is a great interest in synthetic methods directed toward the creation of large collections (libraries) of small organic compounds which could be screened for pharmacological activity. Often referred to as combinatorial chemistry, the synthetic methods applied to create vast combinatorial libraries are performed in solution or on the solid phase. Solid-phase synthesis makes it easier to conduct multistep reactions and to drive reactions to completion, because excess reagents can be added and easily washed away after each reaction step. Solid-phase combinatorial synthesis also makes isolation, purification or screening more manageable. However, more traditional solution phase chemistry supports a wider variety of organic reactions than the solid-phase. Typically, combinatorial methods involve selection of various structural components which are used to modify a core chemical structure. One adds individual structural components as part of a chemical synthesis sequentially, either in a controlled or random manner, to produce all or a substantial portion of the possible compounds that can result from the different choices possible at each sequential stage in the synthesis. Efficient use of this technique can create thousands of compounds for pharmacological screening in a short period of time.

Methods for screening libraries of compounds for binding properties to a receptor include methods wherein each member of the library is tagged with a unique identifier to facilitate identification of compounds having binding properties, and methods wherein the library comprises a plurality of compounds synthesized at particular locations on the surface of a solid substrate. The receptor may be appropriately labelled with a radioactive or fluorescent label that enables one to ascertain whether binding to the receptor of interest has occurred. Correlation of the labelled receptor bound to the substrate with its location on the substrate identifies the binding ligand as described in U.S. Pat. No. 5,143,854.

In contrast to the standard combinatorial chemistry approach which results in libraries with maximum diversity, there is a trend toward the design of more targeted libraries which minimize redundancy and improve screening efficiency.

One particular class of compounds that would be useful for inclusion in targeted libraries is quinazolinone compounds, including dihydro-quinazolinones and derivatives thereof. This class of compounds possesses a diverse array of pharmaceutical and chemical properties. For example, dihydro-quinazolinones are known to possess antipyretic, hypotensive, antibacterial, antifungal or Central Nervous System ("CNS") depressant activity as well as the ability to inhibit enzymes of biological importance, for example, metalloenzymes.

Bonola et al. (J. Med. Chem., 13, 329–332 (1970)) describe the synthesis of 2,3-dihydro-4(1H)-quinazolinone derivatives of the following formula:

where R is hydrogen, hydroxy, phenyl, substituted phenyl, and furyl and $R^1$ is hydroxy, alkoxy, anilino, alkylamino, and alkyl (dialkylamino). These compounds are made by condensation of an appropriately substituted amine with isatoic anhydride. The corresponding aminobenzamide is then condensed with the appropriate aldehyde or ketone to yield a dihydro-quinazolinone. Alternatively, the condensation of 2-aminobenzohydroxamic acid with the appropriate aldehyde or ketone leads to the corresponding N-hydroxy-dihydroquinazolinone. Notably, all of the dihydroquinazolinones described above are prepared under neutral or basic conditions in alcoholic solvents or alcoholic solvents containing an alkoxide or amine base.

Christie et al. (J. Chem. Soc. Perkin Trans. I, 2779–2783 (1985)) describe the synthesis of dihydro-quinazolinones and N-hydroxy-quinazolinones by the reaction of the appropriate aminobenzamide or aminobenzohydroxamic acid with the appropriate corresponding aldehyde or ketone in an alcoholic solvent.

However, a simple procedure for synthesizing a multiplicity of quinazolinones on a variety of solid supports would create a combinatorial library, enhance the structural variation of the pharmacophore and provide the opportunity to evaluate the library through pharmacological screening to obtain important structure-activity information and potential drug candidates.

Accordingly, there is a clear need in the art for an efficient method for obtaining a library of 2,3-dihydro-quinazolinones, wherein the starting materials are amenable to large scale synthesis, and wherein the desired products can be obtained under relatively mild conditions employing readily available reagents.

Citation or identification of any reference in this section of this application shall not be construed as an admission that such reference is available as prior art to the present application.

3. SUMMARY OF THE INVENTION

It has now been surprisingly found that combinatorial libraries of 3-alkoxy and 3-hydroxy-2,3-dihydro-4(1H)-quinazolinones can be synthesized from the corresponding 2-amino-benzamides bound to a solid support by treatment with a Lewis acid catalyst such as zinc chloride or triflates of the lanthanide series, such as scandium triflate or ytterbium triflate. Previously, dihydro-quinazolinones were formed from 2-aminobenzamides under neutral or basic conditions, and not on a solid support.

The present invention is directed towards methods for synthesizing libraries of dihydro-quinazolinones, particularly 2,3-dihydro-3-alkoxy-4(1H)-quinazolinones or 2,3-dihydro-3-hydroxy-4(1H)quinazolinones via the Lewis-acid catalyzed cyclization of the appropriate 2-aminobenzamide with aldehydes at ambient temperatures. In another aspect, the present invention relates to a method for preparing 2,3-dihydro-3-hydroxy-4(1H)-quinazolinones by the Lewis-acid catalyzed reaction of aldehydes with a 2-amino-3-alkoxybenzamide on a solid support, either in a parallel manner or in a combinatorial fashion followed by the cleavage of the desired products from the solid support.

This invention also provides, in one of its aspects, to general synthetic methods for incorporating a 2,3-dihydro-3-alkoxy-4(1H)-quinazolinone of the following formula (I) onto a solid support.

(I)

wherein $R^1$, $R^2$, $R^3$ and $R^4$ are independently hydrogen, halogen, $C_1$–$C_6$ alkyl, $C_1$–$C_6$ alkenyl, hydroxy, $C_1$–$C_6$ alkoxy, $NO_2$, $SO_2Ph$, phenyl, $SO_2NR^6R^7$, $NR^6R^7$, $OCOR^8$, $SR^8$, $CO_2R^8$, $NHCOR^8$; or $R^1$ and $R^2$, $R^2$ and $R^3$, or $R^3$ and $R^4$ can be taken together to form a 5–7 membered carbocyclic aromatic group or heterocyclic aromatic group wherein the heterocyclic aromatic group is selected from the group consisting of furyl, thienyl, pyridyl, pyrrolyl, oxazolyl, thiazolyl, imidazolyl, pyrazolyl, isoxazolyl, isothiazolyl, pyridazinyl, pyrimidinyl, pyrazinyl, or indolyl;

$R^5$ is hydrogen, $C_1$–$C_6$ alkyl, $C_1$–$C_6$ alkenyl, benzyl, phenyl, $CH_2$-furyl, $CH_2$-pyridyl wherein the alkyl, alkenyl, benzyl, phenyl, furyl and pyridyl groups may be further substituted with substituents independently selected from the group consisting of $C_1$–$C_6$ alkyl, $C_1$–$C_6$ alkoxy, halogen, $NO_2$ $CF_3$ or CN;

$R^6$ and $R^7$ are independently H, $C_1$–$C_6$ alkyl or, taken together are $(CH_2)_f$ where f is 3–6;

$R^8$ is hydrogen, $C_1$–$C_6$ alkyl, benzyl, phenyl, or substituted phenyl with 1–3 substituents independently selected from the group consisting of $C_1$–$C_6$ alkyl, $C$.-$C_6$ alkoxy, $NO_2$, $CF_{31}$ or CN;

$R^9$ is hydrogen, $C_1$–$C_6$ branched or straight alkyl, $C_1$–$C_6$ branched or straight alkenyl, $C_1$–$C_6$ aralkyl, $C_1$–$C_6$ aralkenyl, $C_1$–$C_{10}$ cycloalkenyl, $C_1$–$C_{10}$ bicycloalkenyl, $C_1$–$C_6$ cycloalkyl, phenyl, phenyl substituted with 1–3 substituents independently selected from the group consisting of halogen, $C_1$–$C_6$ alkyl, $C_1$–$C_6$ alkoxy, $SR^8$, $OR^8$, $CF_3$, $OCF_3$ or $NO_2$, a 5–10 membered carbocyclic aromatic group or heterocyclic aromatic group wherein the heterocyclic group is selected from the group consisting of furyl, thienyl, pyridyl, pyrrolyl, oxazolyl, thiazolyl, imidazolyl, pyrazolyl, isoxazolyl, isothiazolyl, pyridazinyl, pyrimidinyl, pyrazinyl, or indolyl where the heterocyclic aromatic group can be further substituted with a phenyl group which may be substituted with 1–3 substituents independently selected from the group consisting of $CF_3$, halogen, $C_1$–$C_6$ alkyl, $C_1$–$C_6$ alkoxy, or $OCOR^8$;

J is N or CH with the proviso that when J is N, $R^4$ is not a substituent; and

Y is an appropriate cleavable linker such as —O—$CH_2$, linked to a suitable solid support.

Solid state methods can be employed along with known solution techniques to prepare libraries containing the dihydro-quinazolinone group.

Solid supports containing the dihydro-quinazolinone group comprise a cleavable linker or linking arm which links the solid support to the compound. The linking arm can be an alkyleneoxy or aryleneoxy ether moiety which is cleavable by treatment with an organic or inorganic acid yielding the free 2,3-dihydro-3-hydroxy-4(1H)-quinazolinone. The library of compounds that can be generated on the solid support comprises a diverse array of substituted dihydroquinazolinones, that once cleaved, can be screened to identify and/or isolate individual compounds that bind to a specific protein or receptor or possess some desired pharmacological or chemical property such as antibacterial or antifungal activity. In a preferred embodiment, each compound in the library is novel.

This invention is directed to a method of synthesizing a 2,3-dihydro-3-hydroxy-4(1H)-quinazolinone using a solid support which comprises reacting the O-protected hydroxylamine (wherein the oxygen of hydroxylamine is bound to the solid support) derivatized solid support with an appropriate isatoic anhydride and cyclizing the resultant 2-aminobenzamide to the desired 2,3-dihydro-3-hydroxy-4 (1H)-quinazolinone in the presence of a Lewis acid catalyst.

Further, this invention provides a method of synthesizing novel 2,3-dihydro-3-hydroxy-4(1H)-quinazolinones from a solid support bound precursor which method comprises:

(a) selecting a solid support comprising at least one compound covalently attached to said solid support which compound comprises an O-protected hydroxylamine;

(b) reacting said moiety of said compound covalently attached to said solid support with a diverse array of isatoic anhydrides to yield a 2-aminobenzamide;

(c) reacting the corresponding 2-aminobenzamide with an aldehyde in the presence of a Lewis acid catalyst to yield a 2,3-dihydro-3-alkoxy-4(1H)-quinazolinone.

The resulting 2,3-dihydro-3-alkoxy--4(1H)-quinazolinone is bound to said solid support and may optionally be removed under acidic conditions. Further, it is preferred that step (b) above be conducted in an aprotic solvent at temperatures from about 50 degrees Celsius to about 90 degrees Celsius. Moreover, it is preferred that step (c) be conducted in an inert solvent at about room temperature.

Further, the invention is directed to a method for synthesizing 2,3-dihydro-3-alkoxy-4(1H)-quinazolinones in solution which method comprises:

The reaction of a 2-amino-N-alkoxy benzamide or 2-amino-N-hydroxy-benzamide with an aldehyde in the presence of a Lewis acid catalyst. This reaction can be carried out at a variety of temperatures and in an aprotic organic solvent.

5. DETAILED DESCRIPTION OF THE INVENTION

The present invention provides a reliable, high yielding solution phase reaction of 2-amino-3-alkoxybenzamides to 2,3-dihydro-3-hydroxy-quinazolinones or 2,3-dihydro-3-alkoxy-quinazolinones via a Lewis-acid catalyzed cyclization with a suitable aldehyde. Suitable aldehydes include, but are not limited to, those of the formula (V) ($R^9CHO$) where $R^9$ is as previously defined. As a result of the reaction design, as well as its reliability and yield, this synthetic approach can also be run on a solid support. This solid-phase synthetic method facilitates assembly of combinatorial libraries of the dihydro-quinazolinone pharmacophore. This is turn allows for rapid and efficient screening of tens, hundreds, and up to thousands of dihydro-quinazolinones for pharmacological activity. The solid-phase or resin bound molecules can also be further substituted or simply isolated and screened.

The products of the method of this invention are organic compounds. Synthesis involves addition or removal of chemical units, reactions involving the modification or introduction of one or more functionalities, ring openings, ring closings, etc. Chemical units can take many forms, both naturally-occurring and synthetic, such as nucleophiles, electrophiles, dienes, alkylating or acylating agents, diamines, nucleotides, amino acids, sugars, lipids, or derivatives thereof, organic monomers, and combinations thereof. Alternatively, reactions may be involved which result in alkylation, acylation, nitration, halogenation, oxidation, reduction, hydrolysis, substitution, elimination, addition, and the like.

Reactions may involve modifications at a variety of sites of a central core molecular structure or modifications at a specific site. For example, a polycyclic compound may be brominated at a plurality of sites or at a particular site. For the most part, reactions involve single sites or equivalent sites, for example, one of two hydroxyl groups of a glycol.

The synthetic strategies applied with connection with the methods of the invention vary with the nature of the products. Thus, the strategy must take into consideration the ability to change the nature of the product, while allowing for retention of the results of previous synthetic steps and anticipating needs for future steps. Those skilled in the art will look to the nature of the individual unit and either synthetic opportunities will be known or will be devised, as appropriate.

A variety of reaction conditions may be used during the combinatorial synthesis, involving differences in solvent, temperatures, times, concentrations, and the like. Batch synthesis of a few compounds to be prepared during the course of the combinatorial synthesis can be used to optimize conditions and enhance yields of compounds which might not otherwise be formed or be formed only in low yield. Furthermore, one may use batch syntheses to develop assays to characterize the activity of the compounds.

The present invention provides, in one of its aspects, a solid phase reaction component comprising a solid support substantially insoluble in aqueous or organic reaction media, carrying a plurality of covalently bound hydroxylamines where the amine moiety is available for reaction with a substrate and the hydroxyl moiety is covalently linked to the residue of the solid support and is cleavable under acidic conditions, by photolysis or other methods.

Suitable solid supports include those known in the art of solid phase small molecule and peptide synthesis (see for example those described in Stewart J M and Young J D, Solid Phase Peptide Synthesis, 2nd Ed.; Pierce Chemical Company; Rockford, Ill., 1984). These include, but are not limited to, inorganic substrates, for example, kieselguhr, silica gel and controlled pore glass, and polymeric organic substrates, for example, polystyrene, polypropylene, polethyleneglycol, polyacrylamide, cellulose, as well as composite inorganic/polymeric substrates such as polyacrylamide supported within a matrix of kieselguhr particles. Such known solid supports include amino and hydroxy functionalized solid supports, such as those which are chemically modified by introduction of amino or hydroxyl groups, to serve as convenient points for further chemical manipulation.

The solid phase reaction components of the present invention may comprise a solid support, as described above, and a cleavable linker or linker arm which presents the amine moiety of the hydroxylamine group for reaction with the first reactive entity in the proposed synthesis.

As used in this application, the term "linker" means a chemical moiety which may possess a variety of properties. First, it is attachable to a solid support. Second, it is cleavable from the solid support such that when it is cleaved, the desired compound may be released from the solid support. These properties may be embodied by a single chemical structure. Alternatively, these properties may be embodied in multiple chemical structures which are linked together by covalent bonds or by other means.

When detachment of the product is desired, there are numerous suitable functionalities and reactants which may be used. Conveniently, ethers may be used, where substituted benzyl ether or derivatives thereof, e.g., benzhydryl ether, indanyl ether, etc. may be cleaved by acidic or mild reductive conditions. Alternatively, β-elimination may be used, where a mild base may serve to release the product. Acetals, including the thio analogs thereof, are also suitable where mild acid, particularly in the presence of a capturing carbonyl compound, may serve. By combining formaldehyde, HCl and an alcohol, an α-chloroether is formed. This may then be coupled with an hydroxy functionality on the solid support to form the acetal. Various photolabile linkages may be employed, such as o-nitrobenzyl, 7-nitroindanyl, 2-nitrobenzhydryl ethers or esters, etc. Esters and amides may serve as linkers, where half-acid esters or amides are formed, particularly with cyclic anhydrides, followed by reaction with hydroxyl or amino functionalities on the solid support, using a coupling agent such as a carbodiimide. Peptides may be used as linkers, where the sequence is subject to enzymatic hydrolysis, particularly where the coenzyme recognizes a specific sequence. Carbonates and carbamates may be prepared using carbonic acid, base or a strong reductant, e.g., $LiAlH_4$, particularly for the carbonate esters. For a list of cleavable linkers, see for example, Greene and Wuts, Protective Groups in Organic Synthesis, 2nd ed. Wiley, 1991. The versatility of the various systems allows for broad variation in the conditions for attachment of products and identifiers and differential detachment of products.

5.1. Solid-Phase Synthesis of 2,3-dihydro-quinazolinones

Figure 2:
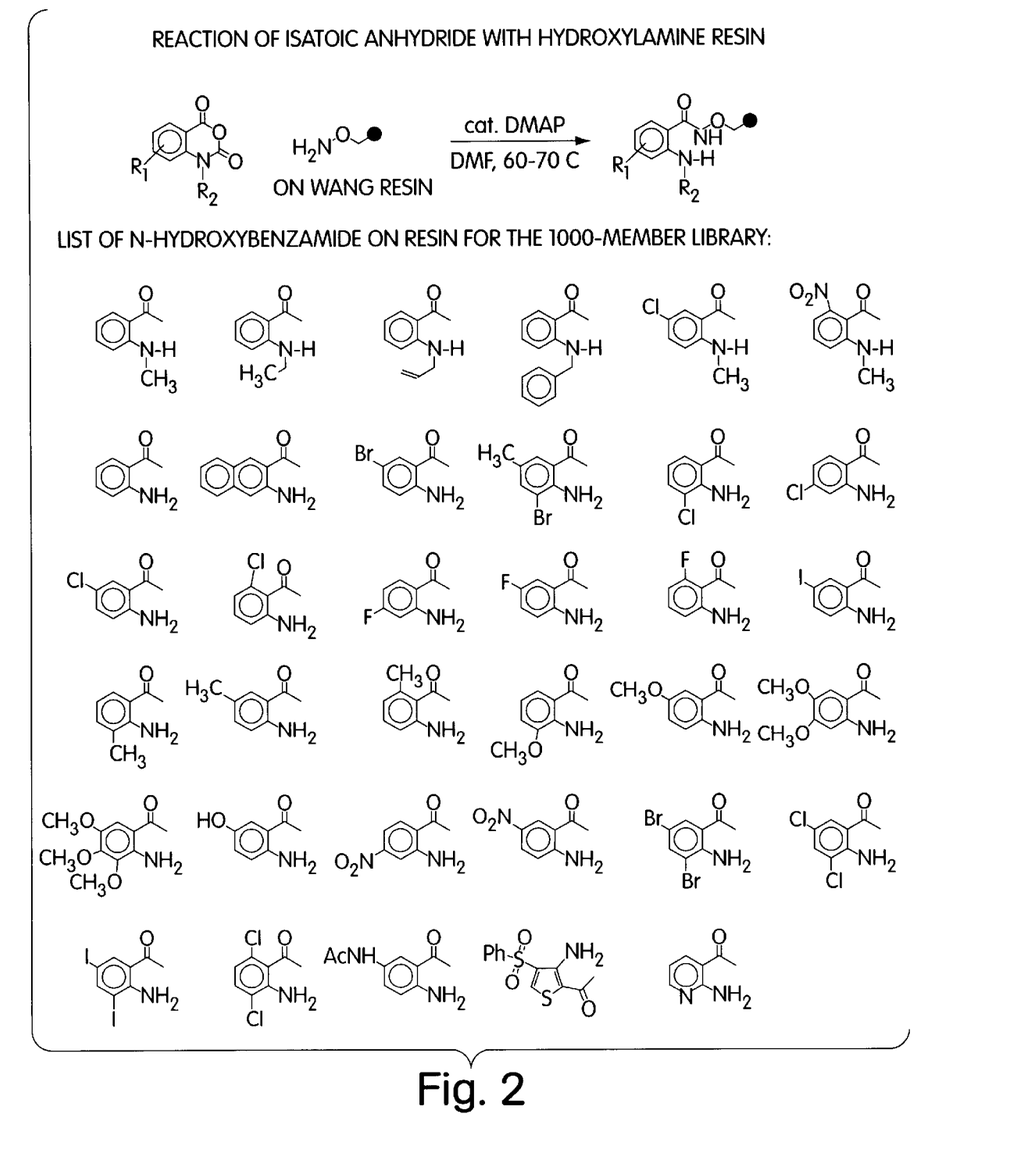
FIG. 2 illustrates the preparation of 2-amino benzamides in the solid phase from the reaction of isatoic anhydrides with hydroxylamine bound to a solid support. The corresponding 2-aminobenzamides bound to the solid support were used to prepare the library of 2,3-dihydro-3-hydroxy-4(1H)-quinazolinones.

The solid-phase reaction components of the invention above will generally be accessible (i) by displacement of a leaving group (e.g., a triflate, mesylate, or halogen group) on the solid support by N-hydroxyphthalimide in the presence of triphenyl phosphine and diethyl azodicarboxylate followed by (ii) removal of the phthalimide protecting group with hydrazine hydrate affording an O-solid supported N-hydroxylamine.

Figure 1:
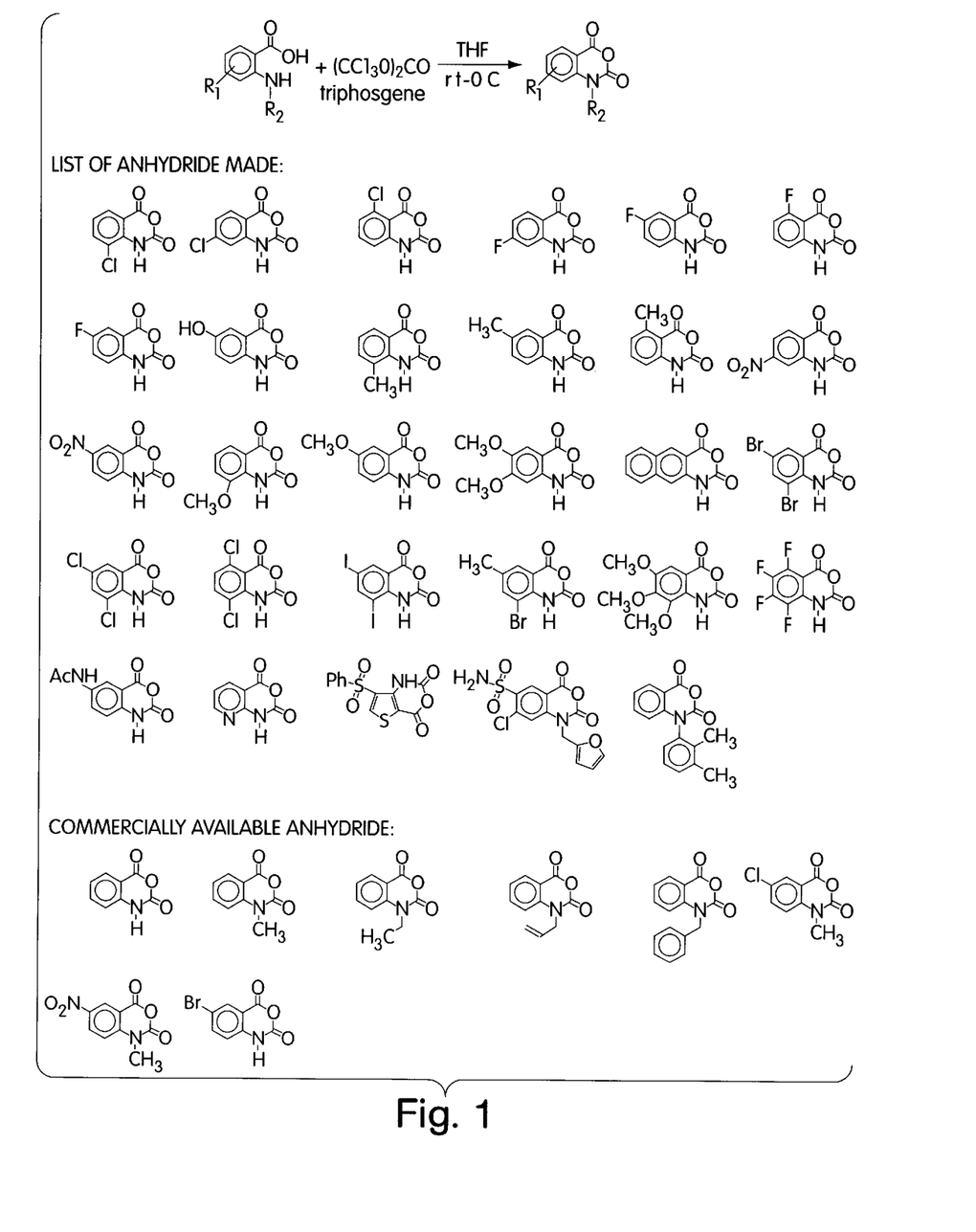
FIG. 1 shows some commercially available isatoic anhydrides and illustrates the preparation of a series of isatoic anhydrides from the reaction of substituted anthranilic acids with triphosgene.

The amine moiety of the O-solid supported N-hydroxyl amine is then reacted with a diverse array of isatoic anhydrides to produce the corresponding 2-amino-N-hydroxybenzamides bound to the solid support. The isatoic anhydrides are either commercially available (e.g. Aldrich Chemical Co.) or may be generally synthesized from reacting a diverse array of anthranilic acids with triphosgene in tetrahydrofuran at room temperature followed by cooling to 0° C. to precipitate the desired isatoic anhydride. For example, treatment of the isatoic anhydride with the O-solid supported N-hydroxyl amine in the presence of a basic catalyst such as dimethylaminopyridine (DMAP) in dry dimethylformamide at about 60–70° C. for about 10 to about 60 hours afforded the corresponding 2-amino-N-alkoxybenzamide on the solid support.

A preferred embodiment of this aspect of the invention is a solid phase reaction component, comprising a solid support, substantially insoluble in aqueous or organic reaction media, carrying a plurality of groups of formula (II):

(II)

wherein $R^1$, $R^2$, $R^3$ and $R^4$ are independently hydrogen, halogen, $C_1$–$C_6$ alkyl, $C_1$–$C_6$ alkenyl, hydroxy, $C_1$–$C_6$ alkoxy, $NO_2$, $SO_2Ph$, phenyl, $SO_2NR^6R^7$, $NR^6R^7$, $OCOR^8$, $SR^8$, $CO_2R^8$, $NHCOR^8$ or $R^1$ and $R^2$, $R^2$ and $R^3$, or $R^3$ and $R^4$ can be taken together to form a 5–7 membered carbocyclic aromatic group or heterocyclic aromatic group wherein the heterocyclic aromatic group is selected from the group consisting of furyl, thienyl, pyridyl, pyrrolyl, oxazolyl, thiazolyl, imidazolyl, pyrazolyl, isoxazolyl, isothiazolyl, pyridazinyl, pyrimidinyl, pyrazinyl, or indolyl;

$R^5$ is hydrogen, $C_1$–$C_6$ alkyl, $C_1$–$C_6$ alkenyl, benzyl, phenyl, $CH_2$-furyl, $CH_2$-pyridyl, wherein the alkyl, alkenyl, benzyl, phenyl, furyl and pyridyl groups may be further substituted with substituents independently selected from the group consisting of $C_1$–$C_6$ alkyl, $C_1$–$C_6$ alkoxy, halogen, $NO_2$, $CF_3$, or $CN$;

$R^6$ and $R^7$ are independently H, $C_1$–$C_6$ alkyl or, taken together are $(CH_2)_f$ where f is 3–6;

$R^8$ is hydrogen, $C_1$–$C_6$ alkyl, or phenyl or substituted phenyl with 1–3 substituents independently selected from the group consisting of $C_1$–$C_6$ alkyl, $C_1$–$C_6$ alkoxy, $NO_2$, $CF_3$, or $CN$;

J is N or CH with the proviso that when J is N, $R^4$ is not a substituent; and

Y is an appropriate cleavable linker such as an —O—$CH_2$—, linked to a suitable solid support.

In this embodiment, compounds of the formula (II) are linked to the solid support via "Y", defined as —O—$CH_2$— where the oxygen atom in —O—$CH_2$ is bound to the nitrogen atom bearing the "Y" substituent in Formula (II). It will be apparent that these "Y" groups may be incorporated during synthesis of the solid phase reaction component of the invention by starting with a solid support such as hydroxymethyl polystyrene, 4-(hydroxymethyl) phenoxymethyl-copoly (styrene-1% divinyl benzene)-resin (100–200 mesh, "Wang" resin), hydroxymethyl copoly (styrene — 1% divinylbenzene), benzhydrylaminepolystyrene, benzyhydrylamine copoly (styrene—1% divinylbenzene ("BHA Resin"), methyl benzhydydryl aminepolystyrene, methyl benzhydrylamine copoly (styrene—1% divinylbenzene ("MBHA Resin"); polyethylene glycol polystyrene ("PEG-PS"); poly (dimethylacrylamide) polystyrene composite ("Polyhipe"); polyacrylamide Kieselguhr composite ("Macrosorb"); or functionalized controlled pore glass.

As used herein the term "$C_1$–$C_6$ alkyl" means a straight or branched chain alkyl moiety having from 1 to 6 atoms, including for example, methyl, ethyl, n-propyl, isopropyl, n-butyl, isobutyl, sec-butyl, t-butyl, pentyl and hexyl. The term "$C_1$–$C_6$ alkoxy" means an alkoxy group wherein the alkyl part is $C_1$–$C_6$ alkyl.

The term "halogen" means bromine, iodine, fluorine or chlorine. The term "$C_1$–$C_6$ aralkyl" means a straight or branched chain alkyl moiety having from 1–6 atoms bearing a phenyl substituent at any carbon in the chain. The term "$C_1$–$C_6$ aralkenyl" means a straight or branched chain alkenyl moiety having from 1–6 atoms bearing a phenyl substituent at any carbon in the chain.

The preferred solid supports are the Wang Resin and the BHA resin. Most preferred as a solid support for the solid phase reaction is 4-(Hydroxymethyl) phenoxymethyl-copoly (styrene—1% divinyl benzene)-resin (100–200 mesh, "Wang" resin).

The choice of solvent for syntheses based on a solid phase reaction component of the invention depends on the nature of the reagents to be reacted with such component and the nature of that component. For example, depending upon the aldehyde used in the formation of compounds of formula (I), the selected solvent will vary according to the solubility of the selected aldehyde. In general, aprotic organic solvents are most suitable for the formation of compounds of the formula (I).

Preferred solvents include tetrahydrofuran, acetonitrile and chlorinated solvents such as methylene chloride and 1,2-dichloroethane.

The formation of compounds of formula (I) bound to the solid support is conducted in the presence of an appropriate aldehyde and a Lewis acid catalyst. Suitable Lewis acid catalysts include zinc chloride, boron trifluoride, ytterbium triflate, scandium triflate, and other lanthanide triflates.

The reaction is conducted from about 20 to about 50° Celsius (°C) and preferably from about 20 to about 25° C.

In another of its aspects, the present invention comprises a process for preparing a desired synthetic product whose structure is characterized by the presence of an N-hydroxyl moiety of the formula (III) wherein $R^1$–$R^9$ and J are as previously defined.

(III)

The 2,3-dihydro-3-hydroxy-4(1H)-quinazolinones of formula (III) are produced from the cleavage of the compound of formula (I) from its solid support. Aqueous trifluoroacetic acid or a mixture of trifluoroacetic acid and an organic solvent are generally suitable for the cleavage of the covalent bond between the compounds of formula (I) and the solid support. Preferred hydrolysis conditions include, but are not limited to, trifluoroacetic acid ranging from about 20% v/v to about 95% v/v in methylene chloride. Suitable organic solvents include, but are not limited to, dichloromethane and 1,2-dichloroethane.

The 2,3-dihydro-3-hydroxy-4(1H)-quinazolinones thus produced may be isolated as a trifluoroacetic acid salt. Examples of other acceptable salts include, but are not limited to, hydrochloride, sulfate, hydrogen sulfate, phosphate, hydrogen phosphate, dihydrogen phosphate, succinate, ascorbate, tartrate, citrate, gluconate, benzoate, maleate, malonate, fumarate, and the like.

5.2 Solution Phase Synthesis of 2,3-dihydroquinazolinones

In yet a further aspect of this invention, a combinatorial library of compounds of the formula (IV) is available via solution phase chemistry:

(IV)

wherein $R^1$–$R^9$, and J are as previously defined and $R^{10}$ is H, $C_1$–$C_6$ alkyl, $C_1$–$C_6$ alkenyl, phenyl or phenyl substituted with substituents independently selected from the group consisting of $C_1$–$C_6$ alkyl, $C_1$–$C_6$ alkoxy, $NO_2$, halogen, $CF_3$ or CN.

Figure 3:
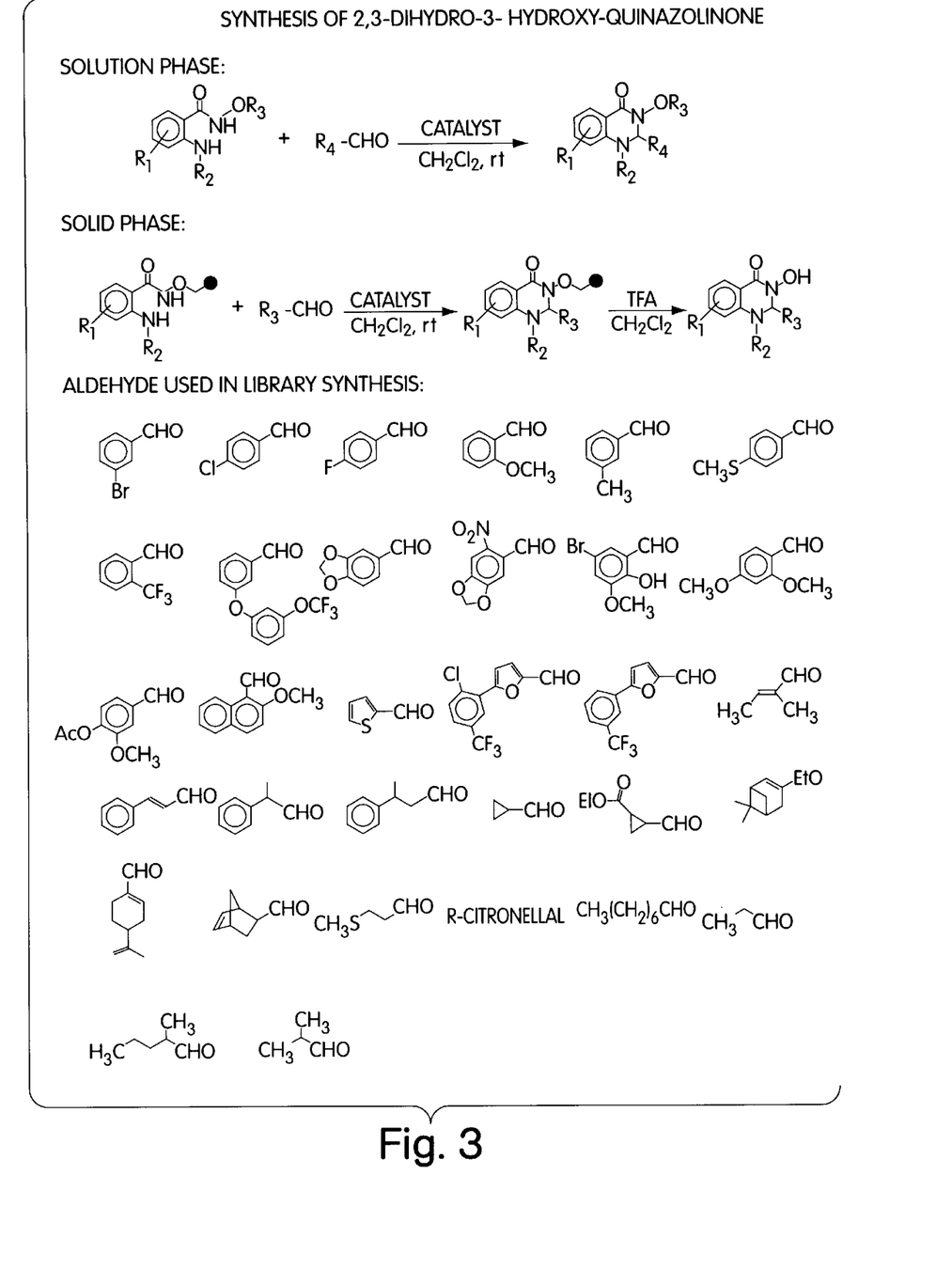
FIG. 3 illustrates the solution phase reaction of a 2 amino-benzamide with an aldehyde in the presence of a Lewis acid catalyst to yield a 2,3-dihydro-3-alkoxy-4(1H)-quinazolinone. It also illustrates the aldehydes used in the preparation of the library of 2,3-dihydro-3-hydroxy-4(1H)-quinazolinones. It further illustrates the solid phase reaction of a 2-aminobenzamide bound to a solid support with an aldehyde in the presence of a Lewis acid catalyst. The product, a 2,3-dihydro-3-alkoxy-4(1H)-quinazolinone is then reacted under aqueous acidic conditions to yield a 2,3-dihydro-3-hydroxy-4(1H)-quinazolinone free of the solid support.

Compounds of the formula (IV) are produced via the following scheme:

A mixture of isatoic anhydride, O-substituted hydroxyl amine hydrochloride and potassium carbonate is stirred at room temperature for about 48 hours to afford a 2-amino-O-substituted benzamide. Suitable substituents for the hydroxyl function of hydroxylamine include, but are not limited to, aryl, alkyl, aralkyl such as benzyl and triphenylmethyl, and alkylaryl groups. The 2-amino-O-substituted benzamide is reacted with an aldehyde ($R^9$CHO, V) in the presence of a Lewis acid at room temperature in an aprotic organic solvent to yield compounds of the formula (IV). Preferred for their reactivity as Lewis acids are zinc chloride, ytterbium triflate and scandium triflate. The preferred aprotic solvents are dichloromethane and 1,2-dichloroethane. Other solvents suitable for effecting the above transformation are acetonitrile, diethylether, tetrahydrofuran, and halogenated solvents, e.g. methylene chloride.

6. EXPERIMENTAL EXAMPLES

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:

| | | |
|---|---|---|
| app d | = | apparent doublet |
| app q | = | apparent quartet |
| app t | = | apparent triplet |
| Ar | = | phenyl |
| br s | = | broad singlet |
| s | = | singlet |
| d | = | doublet |
| dd | = | doublet of doublets |
| DMSO-$d_6$ | = | deuterated dimethyl sulfoxide |
| CDCl$_3$ | = | deuterated chloroform |
| $^1$H NMR | = | proton nuclear magnetic resonance |
| m | = | multiplet |
| MHz | = | megahertz |
| mL | = | milliliter |
| rt | = | room temperature |
| mmol | = | millimole |
| TFA | = | trifluoroacetic acid |
| THF | = | tetrahydrofuran |
| DMF | = | dimethylformamide |
| EtOAc | = | ethyl acetate |
| DMAP | = | dimethylaminopyridine |

Additionally, the Wang resin described herein is commercially available from Aldrich Chemical Co., Milwaukee, Wis. Also, the isatoic anhydrides described herein are available from Aldrich Chemical Co. or may be synthesized according to the procedures described herein.

General Procedure for the Reaction of Isatoic Anhydride with Solid-Supported hydroxylamine A mixture of an isatoic anhydride (3.6 mmol) and O-hydroxylamine on Wang resin (0.6 g, 1.19 mmol/g loading) and DMAP (0.18 mmol) in ca. 8–10 mL of dry DMF was stirred at 60–70° C. for 2.5 days. The mixture was then washed with DMF, CH$_3$OH and CH$_2$Cl$_2$ to give O-resin supported 2-amino-N-hydroxylbenzamide. A sample of the resin was cleaved with trifluoroacetic acid (TFA) in CH$_2$C$_{12}$ (1:1 V/V) to give the corresponding 2-amino-N-hydroxylbenzamide to confirm the attachment to the resin.

Thirty-Five (35) isatoic anhydrides were reacted with the hydroxylamine resin for further synthetic transformations.

General Procedure for the Preparation of Isatoic Anhydride

An ice-cold solution of triphosgene (3.0 g, 10 mmol, 0.4 eq) in 10 mL of anhydrous THF was added to a mixture or solution of anthranilic acid (or 2-amino-benzoic acid) (25 mmol) in 15 mL of dry THF and cooled slowly. The mixture as then stirred or shaken for 24–48 h at room temperature nd cooled in a refrigerator (0° C. to –10° C.) for 12–24 h. The resulting solid was collected by filtration and washed with cold methyl t-butyl ether (MTBE) and dried to give the isatoic anhydride in 70–98% yield. About 30 isatoic anhydrides were prepared in this manner.

Preparation of O-Solid-Supported N-hydroxylamine on Wang Resin

Triphenyl phosphine (28.2 g, 108 mmol) was dissolved in 300 mL of dry THF. To the solution was added Wang resin (25 g, 0.86 mmol/g loading, 100–200 mesh) and N-hydroxyphthalimide was dissolved. The mixture was then cooled with ice-water and a cold solution of diethyl azodicarboxylate (17 mL, 108 mmol) in 20 mL of dry THF was added slowly with shaking and cooling. After addition, the resulting mixture was shaken at rt for 18 h. The mixture was then washed with THF, DMF, CH$_3$OH and CH$_2$Cl$_2$ thoroughly. The washed resin was then suspended in 300 rL of DMF and cooled with ice-water. Hydrazine hydrate (27 mL, 540 mmol) was then added. The mixture was shaken at rt for 16 h and then washed with DMF, CH$_3$OH and CH$_2$Cl$_2$ thoroughly and dried under vacuum to give the O-resin supported hydroxylamine (ca. 25 g).

General Procedure for the Preparation of 2,3-dimydro-3-hydroxy-4(1H)-quinazolinone Via the Solid-Support Reaction

EXAMPLE 1

(a) A suspension of 2-amino-N-hydroxylbenzamide on Wang resin (30 mg, 0.69 mmol/g loading) and p-anisaldehyde (0.013 mL, 0.1 mmol) in 0.5 mL of CH$_2$Cl$_2$ in the presence of ZnCl$_2$/THF solution (0.08 mL, 0.5 M conc.) or Sc(OTf)$_3$ (10 mg) or Yb(OTF)$_3$ (12 mg) was shaken at rm for 20 h. The resin was then washed with CH$_2$Cl$_2$, MeOH and finally CH$_2$Cl$_2$ several times and dried. The resulting 2,3-dihydro-3-hydroxy-4(1H)-quinazolinone on resin was then cleaved with TFA/CH$_2$Cl$_2$ (1:1, ca. 0.2 mL) to give the corresponding 2-p-methoxyphenyl-2,3-dihydro-3-hydroxyquinazolinone after drying as a TFA salt.

The product was confirmed by HPLC, MS and $^1$H NMR analysis.

EXAMPLE 7

In a same manner as Example 1,2-p-methoxyphenyl-6-nitro-2,3-dihydro-3-hydroxyquinazolinone was prepared in 80% yield (14 mg) as TFA salt from 2-amino-5-nitro-N-hydroxybenzamide on resin (60 mg, 0.69 mmol/g loading, 0.04 mmol) and p-anisaldehyde (0.026 mL, 0.4 mmol) using Yb(OTf)$_3$ (12 mg, 0.5 eq to resin loading) as the catalyst, $^1$H NMR (CDCl$_3$, 300 MHz): δ 3.8 (s, 3H), 6.05 (s, 1H), 6.65 (d, 1H), 6.85 (d, 2H), 7.4 (d, 2H), 8.0 (d, 1H), 8.6 (s, 1H).

EXAMPLE 8

In a same manner as Example 1,2-(2-phenylethyl)-6-nitro-2,3-dihydro-3-hydroxyquinazolinone was prepared in 94% yield (8 mg) as TFA salt from 2-amino-5-nitro-N-hydroxybenzamide on resin (30 mg, 0.69 mmol/g loading, 0.02 mmol) and 3-phenylpropionaldehyde (13.4 mg, 0.1 mmol) using Yb(OTf)$_3$ (6.2 mg, 0.5 eq to resin loading) as the catalyst.

In a control experiment, no desired product was obtained without catalyst in the reaction.

EXAMPLE 17

In a same manner as Example 1 above, 2-furan-2-methyl-6-chloro-2,3-dihydro-3-hydroxyquinazolinone was prepared as a TFA salt in 90% yield (7 mg) from 2-methylamino-5-chloro-N-hydroxybenzamide on Wang resin (30 mg, 0.69 mmol/g loading, 0.02 mmol) and 2-furaldehyde (9.6 mg, 0.1 mmol) using Yb(OTf)$_3$ (6.2 mg, 0.5 eq to resin loading).

The compounds of Examples 1, 7, 8, and 17 are shown in Table I, as well as other compounds which were prepared or could be prepared using the procedures of the aforementioned examples.

TABLE I (III)

| Ex | R$^1$ | R$^2$ | R$^3$ | R$^4$ | R$^5$ | R$^9$ | J |
|---|---|---|---|---|---|---|---|
| 1 | H | H | H | H | H | 4-methoxyphenyl | CH |
| 2 | H | H | H | H | CH$_2$CH$_3$ | 4-chlorophenyl | CH |
| 3 | H | H | H | H | allyl | 4-fluorophenyl | CH |

TABLE I-continued (III)

| Ex | R¹ | R² | R³ | R⁴ | R⁵ | R⁹ | J |
|---|---|---|---|---|---|---|---|
| 4 | H | H | H | H | benzyl | 2-methoxyphenyl | CH |
| 5 | H | Cl | H | H | CH₃ | 3-tolulyl | CH |
| 6 | H | H | H | H | CH₃ | 3-bromophenyl | CH |
| 7 | H | NO₂ | H | H | CH₃ | 4-methoxyphenyl | CH |
| 8 | H | NO₂ | H | H | H | 2-phenethyl | CH |
| 9 | H | C₁₀H₇ | — | H | H | 3-O-(3'-OCF₃C₆H₄) | CH |
| 10 | H | Br | H | H | H | 2-(1,3-Benzodioxole) | CH |
| 11 | H | CH₃ | H | Br | H | 1-Nitro-2-(1,3 Benzodioxole) | CH |
| 12 | H | H | H | Cl | H | 2-Hydroxy-5-Bromo-3-anisole | CH |
| 13 | H | H | Cl | H | H | 2,4-(dimethoxy)phenyl | CH |
| 14 | H | Cl | H | H | H | 3-methoxy-4 acetylphenyl | CH |
| 15 | Cl | H | H | H | H | 2-(methoxy)naphthyl | CH |
| 16 | H | H | F | H | H | 2-thienyl | CH |
| 17 | H | Cl | H | H | CH₃ | 2-furyl | CH |
| 18 | F | H | H | H | H | 2-(3'-trifluoromethyl-phenyl)-furyl | CH |
| 19 | H | I | H | H | H | cis-2-butenyl | CH |
| 20 | H | H | H | CH₃ | H | cyclopropyl | CH |
| 21 | H | CH₃ | H | H | H | myrtanyl | CH |
| 22 | CH₃ | H | H | H | H | octanyl | CH |
| 23 | H | H | H | OCH₃ | H | ethyl | CH |
| 24 | H | OCH₃ | H | H | H | 2-pentanyl | CH |
| 25 | H | OCH₃ | OCH₃ | H | H | isopropyl | CH |
| 26 | H | OCH₃ | OCH₃ | OCH₃ | H | 2-(thiomethyl)ethyl | CH |
| 27 | H | OH | H | H | H | 2-carbethoxy cyclopropyl | CH |
| 28 | H | H | NO₂ | H | H | trans-cinnamyl | CH |
| 29 | H | NO₂ | H | H | H | 2-(5-norborenyl) | CH |
| 30 | H | Br | H | Br | H | 2-methylphenyl | CH |
| 31 | H | Cl | H | Cl | H | 2-(methyl)phenethyl | CH |
| 32 | H | I | H | I | H | 2-pyrrolyl | CH |
| 33 | H | NHAc | H | H | H | phenyl | CH |
| 34 | H | H | H | — | H | phenyl | N |

General Procedure for the Solution Phase Synthesis of 2,3-dihydro-quinazolinones

EXAMPLE 35
Reaction of Isatoic Anhydride With O-Substituted Hydroxylamine:

(a) Reaction with isatoic anhydride: A mixture of isatoic anhydride (3.3 g, 20 mmol), O-benzylhydroxylamine hydrochloride (4.4 g, 27 mmol) and K₂CO₃ (6.9 g, 50 mmol) in 20 mL of DMF was stirred at rt until all the anhydride was consumed (ca. 2 days) by thin layer chromatographic analysis. The mixture was diluted with MTBE and washed with water and brine. After removal of solvent, the crude product was recrystallized from EtOAc/heptane to give 2-amino-N-benzyloxylbenzamide as a white solid (3.25 g, 67% yield).

EXAMPLE 35
2-(p-methoxyphenyl)-3-benzyloxy-2,3-dihydroquinazolinone:

A solution of 2-amino-N-benzyloxybenzamide (73 mg, 0.3 mmol) and p-methoxybenzaldehyde (61 mg, 0.45 mmol) in 2 ml of CH₂Cl₂ was stirred at room temperature in the presence of Sc(OTf)₃ (15.0 mg, 0.03 mmol). After 24 h, HPLC showed no benzamide was left. The mixture was then diluted with EtOAc and washed with saturated aq. NaHCO₃ and Na₂SO₃ and dried. After removal of solvents, the title product (ca. 106 mg) was obtained as a white solid. In a control experiment, no desired product was obtained without catalyst in the reaction.

EXAMPLE 36(a)

In the same manner as Example 35(a), O-benzylhydroxylamine hydrochloride (1.92 g, 12 mmol) reacted with N-methylisatoic anhydride (2.0 g, 10 mmol) to give 2-methylamino-N-benzyloxylbenzamide as a yellow solid (0.75 g).

EXAMPLE 36(b)
1-Methyl-2-(p-methoxyphenyl)-3-benzyloxy-2,3-dihydroquinazolinone:

This compound was prepared in the same manner as Example 35(b) above in >95% yield.

EXAMPLE 37(a)

In the same manner as Example 35(a), O-benzylhydroxylamine hydrochloride (1.92 g, 12 mmol) reacted with N-methyl-5-chloro-isatoic anhydride (2.13 g, 10 mmol) to give 2-methylamino-5 chloro-N-benzyloxylbenzamide as a white solid (1.47 g).

EXAMPLE 37(b)
1-Methyl-2-(p-methoxyphenyl)-3-benzyloxy-6-chloro-2,3-dihydroquinazolinone:

This compound was prepared in a same manner as Example 35(b) above after 48 h of reaction in >95% yield.

EXAMPLE 38(a)

In the same manner as Example 35(a), O-benzylhydroxylamine hydrochloride (0.52 g, 3.25 mmol) reacted with 5-nitro-isatoic anhydride (0.52 g, 2.5 mmol) to give 2-amino-5-nitro-N-benzyloxylbenzamide as a yellow solid (0.51 g).

EXAMPLE 38(b)
2-(p-Methoxyphenyl)-3-benzyloxy-6-nitro-2,3-dihydroquinazolinone:

A solution of 2-amino-5-nitro-N-benzyloxybenzamide (57 mg, 0.2 mmol) and p-anisaldehyde (0.03 mL, 0.24 mmol) in 1.5 mL of $CH_2Cl_2$ in the presence of 10 mg (0.02 mmol) of $Yb(OTf)_3$ was stirred at rt for 2 days. HPLC showed no benzamide remained. The reaction was worked up as Example-(a) to give the title product as a yellow solid (ca. 75 mg, 95% yield). $^1$H NMR ($CDCl_3$-$DMSO$-$d_6$, 300 Mhz): δ 3.8 (s, 3H), 4.4 (d, 1H), 4.9 (d, 1H), 5.1 (s, 1H), 5.8 (s. 1H), 6.7 (d, 1H), 6.9 (d, 2H), 7.2–7.5 (m, 5H), 7.5 (d, 2H), 8.0 (m, 1H), 8.7 (s, 1H).

The compounds of Example 35–38 are shown in Table II, as well as other compounds that could be prepared using the procedures of the aforementioned examples.

TABLE II (IV)

| Ex | $R^1$ | $R^2$ | $R^3$ | $R^4$ | $R^5$ | $R^9$ | $R^{10}$ | J |
|---|---|---|---|---|---|---|---|---|
| 35 | H | H | H | H | H | p-methoxyphenyl | benzyl | CH |
| 36 | H | H | H | H | Me | p-methoxyphenyl | benzyl | CH |
| 37 | H | Cl | H | H | Me | p-methoxyphenyl | benzyl | CH |
| 38 | H | $NO_2$ | H | H | Me | p-methoxyphenyl | benzyl | CH |
| 39 | H | H | H | H | H | $CH_3$ | benzyl | CH |
| 40 | H | H | H | H | H | allyl | benzyl | CH |
| 41 | H | H | H | H | H | phenyl | benzyl | CH |
| 42 | H | H | H | H | $CH_3$ | 3-bromophenyl | benzyl | CH |
| 43 | H | H | H | H | $CH_2CH_3$ | 4-chlorophenyl | benzyl | CH |
| 44 | H | H | H | H | allyl | 4-fluorophenyl | benzyl | CH |
| 45 | H | H | H | H | benzyl | 2-methoxyphenyl | benzyl | CH |
| 46 | H | Cl | H | H | $CH_3$ | 3-tolulyl | benzyl | CH |
| 47 | H | H | H | H | H | 4-methoxyphenyl | benzyl | CH |
| 48 | $NO_2$ | H | H | H | $CH_3$ | 4-(thiomethyl)phenyl | benzyl | CH |
| 49 | H | H | H | H | H | 4-$CF_3$ | benzyl | CH |
| 50 | H | $C_{10}H_7$ | — | H | H | 3-O-(3'-$OCF_3C_6H_4$) | benzyl | CH |
| 51 | H | Br | H | H | H | 2-(1,3-Benzodioxole) | benzyl | CH |
| 52 | H | $CH_3$ | H | Br | H | 1-Nitro-2-(1,3 Benzodioxole) | benzyl | CH |
| 53 | H | H | H | Cl | H | 2-Hydroxy-5-Bromo-3-anisole | benzyl | CH |
| 54 | H | H | Cl | H | H | 2,4-(dimethoxy)phenyl | benzyl | CH |
| 55 | H | Cl | H | H | H | 3-methoxy-4 acetylphenyl | benzyl | CH |
| 56 | Cl | H | H | H | H | 2-(methoxy)naphthyl | benzyl | CH |
| 57 | H | H | F | H | H | 2-thienyl | benzyl | CH |
| 58 | H | F | H | H | H | 2-furyl | benzyl | CH |
| 59 | F | H | H | H | H | 2-(3'-trifluoromethyl-phenyl)-furyl | benzyl | CH |
| 60 | H | I | H | H | H | cis-2-butenyl | benzyl | CH |
| 61 | H | H | H | $CH_3$ | H | cyclopropyl | benzyl | CH |
| 62 | H | $CH_3$ | H | H | H | myrtanyl | benzyl | CH |
| 63 | $CH_3$ | H | H | H | H | octanyl | benzyl | CH |
| 64 | H | H | H | $OCH_3$ | H | ethyl | benzyl | CH |
| 65 | H | $OCH_3$ | H | H | H | 2-pentanyl | benzyl | CH |
| 66 | H | $OCH_3$ | $OCH_3$ | H | H | isopropyl | benzyl | CH |
| 67 | H | $OCH_3$ | $OCH_3$ | $OCH_3$ | H | 2-(thiomethyl)ethyl | benzyl | CH |
| 68 | H | OH | H | H | H | 2-carbethoxy cyclopropyl | benzyl | CH |
| 69 | H | H | $NO_2$ | H | H | trans-cinnamyl | benzyl | CH |
| 70 | H | $NO_2$ | H | H | H | 2-(5-norborenyly | benzyl | CH |
| 71 | H | Br | H | Br | H | 2-methylphenyl | benzyl | CH |
| 72 | H | Cl | H | Cl | H | 2-(methyl)phenethyl | benzyl | CH |

TABLE II-continued (IV)

| Ex | R¹ | R² | R³ | R⁴ | R⁵ | R⁹ | R¹⁰ | J |
|----|----|----|----|----|----|----|-----|---|
| 73 | H | I | H | I | H | 2-pyrrolyl | benzyl | CH |
| 74 | H | NHAc | H | H | H | phenyl | benzyl | CH |
| 75 | H | H | H | — | H | phenyl | benzyl | N |

Preparation of a Library of 2,3-dihydro-3-hydroxyquinazolinones on Solid Support A ca. 1000-compound library of 2,3-dihydro-3-hydroxyquinazolinone was prepared using 36 resin supported 2-amino-N-hydroxybenzamides by combining two resins per well (ca. 38 mg resin per well, 0.05 mmol) and 32 different aldehydes (5.0 eq per well, 0.25 mmol) and Yb(OTf)$_3$.2H$_2$O (0.5 eq, 0.025 mmol per well) as catalyst in CH$_2$Cl$_2$ at rt. The detailed procedure is as follows:

(a) A stock solution (0.034 M concentration) of Yb(OTf)$_3$ (16 g) in 500 mL of CH$_2$Cl$_2$ and 200 EL of THF was prepared. 0.7 mL of this solution was used per well.

(b) A stock solution of 32 aldehydes (4.0 mmol) in 8 mL of CH2Cl2 was prepared. 0.5 mL of each solution was used.

(c) The 36 N-hydroxybenzamides on resin (600 mg each) were divided into 18 groups by combining two resins per group (1.2 g per group). Each group of resin was suspended in 20 mL of CH$_2$Cl$_2$/MeOH (9:1 v/v) solvent and dispersed to a 96 well reaction block equipped with a frit for filtration and washing (purchased from Advanced Chemtech) (3 groups of resin per block). The solvent was then removed and the resin was then washed twice with CH$_2$Cl$_2$ and dried under vacuum.

(d) The solution of Yb(OTf)$_3$ catalyst (0.7 mL per well) was added, followed by 0.5 mL of aldehyde solution per well (3×32 aldehyde group can be used per reaction block). The reaction block was sealed and shaken on a shaker at rt overnight (ca. 20 h on average). Selected samples were taken, cleaved by TFA/CH$_2$Cl$_2$ and analyzed by HPLC and MS to confirm the completion of the reaction before stopping the reaction.

(e) The resin was then washed twice with CH$_2$Cl$_2$, twice with CH$_3$OH and then twice with CH$_2$Cl$_2$ and dried briefly under vacuum.

(f) TFA/CH$_2$Cl$_2$ (1:1, v/v, 1.0 mL) was then added to each well and the block was shaken at rt for 1 h. The resulting solution was then collected and each well was washed with 1 mL of CH$_2$Cl$_2$ to 96 test tubes respectively. The solutions were then transferred to a 96 deep-well plate and evaporated under vacuum to give the corresponding 2,3-dihydro-3-hydroxyquinazolinone as a TFA salt in a two compound per well format for future biological screening.

In this way, 192 compounds were prepared per reaction block. The above procedure was performed a total of six times using 18 different resins and 32 different aldehydes to yield a total of 1152 2,3-dihydro-3-hydroxyquinazolinones as a mixture of two compounds per well.

The present invention is versatile and can be used to prepare libraries of 2,3-dihydro-quinazolinones having biological activity, including, but not limited to, hypotensive, antibacterial, antifungal, antipyretic and CNS depressant activity. The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A method for synthesizing a 2,3-dihydro-4(1H)-quinazoline, comprising the steps of:
    (a) reacting a free amine moiety bound to a solid support with an isatoic anhydride to afford a 2-aminobenzamide bound to said solid support; and
    (b) reacting said 2-aminobenzamide with an aldehyde in the presence of a Lewis acid catalyst to afford a 2,3-dihydro-4(1H)-quinazolinone bound to said solid support.

2. The method of claim 1, which further comprises removing the 2,3-dihydro-4(1H)-quinazolinone from said solid support by acid hydrolysis.

3. A method for synthesizing 2,3-dihydro-3-alkoxy-4 (1H)-quinazolinones, which comprises:
    (a) selecting a solid support comprising an alkoxylamine moiety covalently attached to said solid support;
    (b) reacting said alkoxylamine moiety covalently attached to said solid support with one or more isatoic anhydrides to afford a 2-amino-O-alkyl benzhydroxamic acid covalently attached to said solid support; and
    (c) reacting said 2-amino-O-alkyl benzhydroxamic acid covalently attached to said solid support with one or more aldehydes in the presence of a Lewis acid catalyst to afford a 2,3-dihydro-3-alkoxy-4(1H)-quinazolinone covalently attached to said solid support.

4. The method according to claim 3, which further comprises:
    (a) reacting said 2,3-dihydro-3-alkoxy-4(1H)-quinazolinone covalently attached to said solid support under acidic hydrolysis conditions to yield a 2,3-dihydro-3-hydroxy-4(1H)-quinazolinone of the formula (III):

(III)

wherein
$R^1$, $R^2$, R3 and $R^4$ are independently hydrogen, halogen, $C_1$–$C_6$ alkyl, $C_1$–$C_6$ alkenyl, hydroxy, $C_1$–$C_6$ alkoxy, $NO_2$, $SO_2Ph$, phenyl, $SO_2NR^6R^7$, $NR^6R^7$, $OCOR^8$, $SR^8$, $CO_2R^8$, $NHCOR^8$; or $R^1$ and $R^2$, $R^2$ and $R^3$, or $R^3$ and $R^4$ can be taken together to form a 5–7 membered carbocyclic aromatic group or heterocyclic aromatic group wherein the heterocyclic aromatic group is selected from the group consisting of furyl, thienyl, pyridyl, pyrrolyl, oxazolyl, thiazolyl, imidazolyl, pyrazolyl, isoxazolyl, isothiazolyl, pyridazinyl, pyrimidinyl, pyrazinyl, and indolyl;

$R^9$ is hydrogen, $C_1$–$C_6$ alkyl, $C_1$–$C_6$ alkenyl, benzyl, phenyl, $CH_2$-furyl, or $CH_2$-pyridyl, wherein the alkyl, alkenyl, benzyl, phenyl, furyl and pyridyl groups may be further substituted with substituents independently selected from the group consisting of $C_1$–$C_6$ alkyl, $C_1$–$C_6$ alkoxy, halogen, $NO_2$, $CF_3$, and CN;

$R^6$ and $R^7$ are independently H, or $C_1$–$C_6$ alkyl, or taken together are $(CH_2)_f$, wherein f is 3–6;

$R^8$ is hydrogen, $C_1$–$C_6$ alkyl, benzyl, phenyl, or substituted phenyl with 1–3 substituents independently selected from the group consisting of $C_1$–$C_6$ alkyl, $C_1$–$C_6$ alkoxy, halogen, $NO_2$, $CF_3$, and CN;

$R^9$ is hydrogen, $C_1$–$C_6$ branched or straight alkyl, $C_1$–$C_6$ branched or straight alkenyl, $C_1$–$C_6$ aralkyl, $C_1$–$C_6$ aralkenyl, $C_1$–$C_{10}$ cycloalkenyl, $C_1$–$C_{10}$ bicycloalkenyl, $C_1$–$C_6$ cycloalkyl, phenyl, phenyl substituted with 1–3 substituents independently selected from the group consisting of halogen, $C_1$–$C_6$ alkyl, $C_1$–$C_6$ alkoxy, $SR^8$, $OR^8$, $CF_3$, $OCF_3$, and $NO_2$, a 5–10 membered carbocyclic aromatic group or heterocyclic aromatic group wherein the heterocyclic group is selected from the group consisting of furyl, thienyl, pyridyl, pyrrolyl, oxazolyl, thiazolyl, imidazolyl, pyrazolyl, isoxazolyl, isothiazolyl, pyridazinyl, pyrimidinyl, pyrazinyl, and indolyl, wherein the heterocyclic aromatic group can be further substituted with a phenyl group which may be substituted with 1–3 substituents independently selected from the group consisting of $CF_3$, halogen, $C_1$–$C_6$ alkyl, $C_1$–$C_6$ alkoxy, and $OCOR^8$; and

J is C.

5. The method according to claim 3 or 4, wherein said alkoxylamine moiety covalently attached to said solid support is hydroxylamine.

6. The method according to claim 3 or 4, wherein said Lewis acid catalyst is selected from the group consisting of zinc chloride, scandium triflate and ytterbium triflate.

7. The method according to claim 4, wherein said acidic hydrolysis conditions comprise trifluoroacetic acid ranging form about 20% v/v to about 95% v/v in methylene chloride.

8. A method of synthesizing 2,3-dihydro-3-alkoxy-4(1H)-quinazolinones of the formula (IV):

(IV)

which comprises:
reacting one or more 2-amino-O-alkyl benzhydroxamic acids with an aldehyde in the presence of a Lewis acid catalyst, wherein said aldehyde has the formula $R^9CHO$;

wherein $R^1$, $R^2$, $R^3$ and $R^4$ are independently hydrogen, halogen, $C_1$–$C_6$ alkyl, $C_1$–$C_6$ alkenyl, hydroxy, $C_1$–$C_6$ alkoxy, $NO_2$, $SO_2Ph$, phenyl, $SO_2NR^6R^7$, $NR^6R^7$, $OCOR^8$, $SR^8$, $CO_2R^8$, $NHCOR^8$; or $R^1$ and $R^2$, $R^2$ and $R^3$, or $R^3$ and $R^4$ can be taken together to form a 5–7 membered carbocyclic aromatic group or heterocyclic aromatic group wherein the heterocyclic aromatic group is selected from the group consisting of furyl, thienyl, pyridyl, pyrrolyl, oxazolyl, thiazolyl, imidazolyl, pyrazolyl, isoxazolyl, isothiazolyl, pyridazinyl, pyrimidinyl, pyrazinyl, and indolyl;

$R^5$ is hydrogen, $C_1$–$C_6$ alkyl, $C_1$–$C_6$ alkenyl, benzyl, phenyl, $CH_2$-furyl, or $CH_2$-pyridyl, wherein the alkyl, alkenyl, benzyl, phenyl, furyl and pyridyl groups may be further substituted with substituents independently selected from the group consisting of $C_1$–$C_6$ alky, $C_1$–$C_6$ alkoxy, halogen, $NO_2$, $CF_3$, and CN;

$R^6$ and $R^7$ are independently H, or $C_1$–$C_6$ alkyl, or taken together are $(CH_2)_f$, wherein f is 3–6;

$R^8$ is hydrogen, $C_1$–$C_6$ alkyl, benzyl, phenyl, or substituted phenyl with 1–3 substituents independently selected from the group consisting of $C_1$–$C_6$ alkyl, $C_1$–$C_6$ alkoxy, halogen, $NO_2$, $CF_3$, and CN;

$R^9$ is hydrogen, $C_1$–$C_6$ branched or straight alkyl, $C_1$–$C_6$ branched or straight alkenyl, $C_1$–$C_6$ aralkyl, $C_1$–$C_6$ aralkenyl, $C_1$–$C_{10}$ cycloalkenyl, $C_1$–$C_{10}$ bicycloalkenyl, $C_1$–$C_6$ cycloalkyl, phenyl, phenyl substituted with 1–3 substituents independently selected from the group consisting of halogen, $C_1$–$C_6$ alkyl, $C_1$–$C_6$ alkoxy, $SR^8$, $OR^8$, $CF_3$, $OCF_3$, and $NO_2$, a 5–10 membered carbocyclic aromatic group or heterocyclic aromatic group wherein the heterocyclic group is selected from the group consisting of furyl, thienyl, pyridyl, pyrrolyl, oxazolyl, thiazolyl, imidazolyl, pyrazolyl, isoxazolyl, isothiazolyl, pyridazinyl, pyrimidinyl, pyrazinyl, and indolyl, wherein the heterocyclic aromatic group can be further substituted with a phenyl group which may be substituted with 1–3 substituents independently selected from the group consisting of $CF_3$, halogen, $C_1$–$C_6$ alkyl, $C_1$–$C_6$ alkoxy, and $OCOR^8$;

$R_{10}$ is H, $C_1$–$C_6$ alkyl, $C_1$–$C_6$ alkenyl, phenyl or phenyl substituted with 1–3 substituents independently selected from the group consisting of $C_1$–$C_6$ alkyl, $C_1$–$C_6$ alkoxy, halogen, $NO_2$, $CF_3$, and CN; and J is C.

9. The method according to claim 8, wherein said Lewis acid is zinc chloride, scandium triflate, or ytterbium triflate.

10. The method according to claim 3, 4, or 8 wherein said Lewis acid is zinc chloride, boron trifluoride, scandium triflate, ytterbium triflate, or any other lanthanide triflate.

* * * * *